United States Patent
Ross, III et al.

(10) Patent No.: US 6,547,391 B2
(45) Date of Patent: Apr. 15, 2003

(54) OCULAR ABERRATION CORRECTION TAKING INTO ACCOUNT FLUCTUATIONS DUE TO BIOPHYSICAL RHYTHMS

(75) Inventors: Denwood F. Ross, III, Jacksonville, FL (US); Brian G. Rice, Jacksonville, FL (US); Tammie M. Braswell, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 152 days.

(21) Appl. No.: 09/732,637

(22) Filed: Dec. 8, 2000

(65) Prior Publication Data

US 2002/0071097 A1 Jun. 13, 2002

(51) Int. Cl.$^7$ ................................................. A61B 3/10
(52) U.S. Cl. ........................................ 351/212; 351/246
(58) Field of Search ................................ 351/211, 212, 351/221, 216, 219, 246, 247, 159, 160 R

(56) References Cited

U.S. PATENT DOCUMENTS

| 6,086,204 A | 7/2000 | Magnante |
| 6,199,986 B1 | 3/2001 | Williams et al. |
| 6,299,311 B1 * | 10/2001 | Williams et al. ............ 351/221 |

FOREIGN PATENT DOCUMENTS

WO     WO 98 27863 A    7/1998

OTHER PUBLICATIONS

Hofer, Heidi et al., "Dynamics of the Eye's Wave Aberration," University of Rochester, USA.

H. Hofer, et al.: "Dynamics of the Eye's Wave Aberration"; Journal of the Optical Society of America—A, Optical Society of America, Mar. 2001, pp. 497–506, vol. 18, No. 3, XP001041247 ISSN: 0740-3232, Washington US.

Charman W. N. et al.: "Fluctuations in Accommodation: a review", Ophthalmic & Physiological Optics, Apr. 1988, pp. 153–164, vol. 8, No. 2, XP008002504 ISSN: 0275-5408, UK.

PCT International Search Report PCT/US01/48245 dated Apr. 25, 2002.

* cited by examiner

*Primary Examiner*—George Manuel
(74) *Attorney, Agent, or Firm*—Lois A. Gianneschi

(57) ABSTRACT

The invention provides correction of wavefront aberrations of the eye that take into account fluctuations in the aberrations due to biophysical rhythms. Correction is provided for an intermediate value of these fluctuations of the wavefront aberrations. This intermediate value is determined by extrapolating a wavefront measurement to predict the overall variation. The final correction is determined using a weighting scheme derived from the clinical comparisons of the frequency and amplitude components of the variations.

14 Claims, No Drawings

OCULAR ABERRATION CORRECTION TAKING INTO ACCOUNT FLUCTUATIONS DUE TO BIOPHYSICAL RHYTHMS

FIELD OF THE INVENTION

The invention relates to ocular aberration correction. In particular, the invention provides correction of wavefront aberrations of the eye that take into account fluctuations in the aberrations due to biophysical rhythms.

BACKGROUND OF THE INVENTION

Techniques and apparatuses for measuring the aberrations of the eye using wavefront sensors are known. The known devices measure, estimate, interpolate, or calculate the ocular optical wavefront. Subsequently, the aberration measurements are mathematically converted to a height difference providing an elevation map above and below a designated mean sphere value, known as the optical path difference. Correction for the aberrations may be provided by introduction of an optical path difference, or aberration inverse filter, that offsets the distortions due to the ocular aberrations. These corrections may be incorporated into the design of an ophthalmic lens to provide visual acuity correction.

A disadvantage of correcting aberrations based on wavefront measurements is that the fluctuations of the aberrations over time caused by biophysical rhythms are not taken into account. Therefore, a need exists for a method of accounting for biophysical rhythms in designing ophthalmic lenses based on wavefront aberration measurements.

DETAILED DESCRIPTION OF THE INVENTION AND PREFERRED EMBODIMENTS

The invention provides a method, and ophthalmic lenses produced using the method, that takes into account fluctuations in ocular wavefront aberration measurements due to biophysical rhythms when computing a correction for those aberrations. The method provides repeatable and reliable measurements for use in determining an accurate correction for the aberrations.

In one embodiment, the invention provides a method of designing a correction for an individual's visual acuity comprising, consisting essentially of, and consisting of the steps of: a.) obtaining, for a computationally sufficient amount of time, an ocular wavefront aberration measurement of the individual's eye; b.) determining a frequency component and an amplitude component for cyclical variations of the ocular wavefront aberration measurements; and c.) computing an ocular wavefront aberration correction for one or more ocular wavefront aberrations of the individual's eye taking into account the cyclical variations. In another embodiment, the invention provides ophthalmic lenses produced using the method of the invention.

By "ophthalmic lens" is meant a spectacle lens, a contact lens, an intraocular lens, an onlay lens, or the like. Preferably, the lenses of the invention are contact lenses. By "ocular wavefront" is meant the wavefront emerging from the eye. By "ocular wavefront aberration" is meant the difference between the wavefront emerging from the eye compared to a perfect wavefront. Apparatuses for performing aberration measurements include, without limitation, aberroscopes, devices that measure ocular Modulation Transfer Function by point or line spread, or any similar devices that measure, estimate, interpolate, or calculate the ocular wavefront The device used must have a sensitivity to enable it to capture variations in aberrations due to biophysical rhythms. Suitable devices are commercially available as, for example, Model G200 from Wavefront Sciences, Inc.

It is a discovery of the invention that cyclical variations, or fluctuations, occur in both high and low order wavefront aberration measurements of an individual's eye that correlate with the biophysical cycles, meaning the circulatory and respiratory cycles, of the individual. Because these variations have no apparent effect on the individual's visual perception, aberration correction must not be performed using the extremes of the variations. Rather, correction must be of an intermediate value of the variations of the wavefront aberrations. This intermediate value is readily determined if the existence of the cyclical variations is assumed and a wavefront measurement is extrapolated using that knowledge to predict the overall variation. The individual's final correction can then be determined using a weighting scheme derived from the clinical comparisons of the frequency and amplitude components of the variations.

In an initial step of the method of the invention, an individual's ocular wavefront aberrations are obtained or measured for a computationally sufficient amount of time. By "computationally sufficient amount of time" is meant that the ocular wavefront aberration measurement is carried out for a period of time sufficient to observe a quantity of wavefront aberration fluctuations due to biophysical cycles, which quantity permits computation of the frequency and amplitude content of the fluctuations. This period of time preferably is sufficient to capture, or for the completion, of at least one complete biophysical cycle, meaning a cycle that contains a complete respiratory and circulatory cycle.

For example, the aberration measurement for an individual may be carried out by capturing 10 images at 5 Hz for purposes of sampling the circulatory, or pulse, cycle effect on wavefront aberrations ; an additional 10 images at 0.3 Hz are captured for purposes of sampling the respiratory cycle effect for a total of 20 images over 35 seconds. Generally, about 20 images over 35 seconds provides at least the minimal amount of data required to compute the frequency and amplitude content of the wavefront variations. However, the specific amount desirable will depend upon the individual being measured.

Alternatively, sufficient samples of ocular wavefront measurements of a population of individuals may be made to determine, generally, the way in which the fluctuations behave. Using this information, one need only carry out ocular wavefront aberration measurements of an unknown individual for a period of time to measure enough wavefront data points on an that individual to determine where, on the curve of variations of the population, that individual falls. Generally, about 5 to about 10 points per each of the respiratory and circulatory cycle will be a sufficient number of points. The remainder of the data required may be inferred from the previous characterizations based on the population sample. For example, the missing points of each cycle may be interpolated or portions of the cycle not measured may be interpolated.

For purposes of the wavefront aberration measurements, the eyes being measured are not dilated or paralyzed. Further, preferably the wavefront data is recorded in the form of images. Software may be used to translate the wavefront images into the appropriate form and to display it in tabular form as it is being recorded. Suitable software includes, without limitation, Complete Light Analysis Software-2D and Complete Ophthalmic Analysis Software available from Wavefront Sciences. The appropriate form selected will depend upon the intended use of the data. For example, the raw data may be translated into Taylor or Zernike polynomials, clinical refractive data computed, and iso-power, 3-dimensional pseudo-color, and optical path difference elevation graphs may be generated.

In the next step of the method of the invention, the frequency and amplitude components for each of the cyclical variations in the ocular wavefront aberration measurements are determined by any convenient method. For example, the aberrations may be represented as Zernike coefficients that are individually subjected to a fast Fourier transform to analyze the way in which the coefficients vary with time. The transform values are then assembled into a histogram and the most probable time from the histogram is the dominant period in that coefficient. In most cases, there will be two periods, one for the fast circulatory rhythm and one for the slower respiratory rhythm. The amplitude is determined directly from the maximum and minimum values of the raw data.

Subsequently, an ocular wavefront aberration correction is computed that takes into account the cyclical variations. In this step, the weighted sums of the individual frequency components are used to derive the aberration correction. Any number of methods may be used to carry this out. For example, all of the measurements may be averaged, or integrated, over the measurement interval. In the simplest form of averaging, images are accumulated, for example 20 images accumulated over 35 seconds. The Zernike terms for the third order terms of defocus, 45 and 90 degree astigmatism, coma-x, coma-y, trefoil astigmatism, and spherical aberration are calculated resulting in 7 sets of 20 data points.

The individual is clinically refracted to obtain actual defocus and astigmatism values and these actual values for visual acuity are compared with the wavefront measured values. This permits definition of the way in which the individual's vision system handles the cyclical variations. Alternately, a population may be refracted to produce data from which an individual's vision system handling of the cyclical variations may be predicted. Only sphere, astigmatism, and angle may be clinically measured. However, it may be assumed that higher order aberrations will be handled by the vision system in he same way.

If the statistical correlation between the clinical data and the wavefront data indicates that the best correlation occurs when the ocular wavefront aberration data, as a function of time is averaged, the arithmetic mean may be calculated for each set and that mean value may be used for aberration correction. Alternatively, the statistical correlation will be used to find another function that best connects the clinical studies with the wavefront data.

The aberration measurements are mathematically converted to a height difference, thus providing an elevation map above and below a designated mean sphere value, known as the optical path difference. Correction for the aberrations will be provided by introduction of an optical path difference, or aberration inverse filter, that offsets the distortions due to the ocular aberrations.

The converted differences may be used to provide the design for an ophthalmic lens for the wearer, for example by input into a lens design program taking into account the optical effect of the correcting lens. The aberration correction may be on either or both the front or back surface of the lens. By "ophthalmic lens" is meant a spectacle lens, a contact lens, an intraocular lens, a corneal implant lens, an onlay lens, and the like, or combinations thereof Preferably, the lenses of the invention are contact lenses. The aberration correction may be on either or both the front or back surface of the ophthalmic lens. Contact lenses useful in the invention may be either hard or soft lenses. Soft contact lenses, made of any material suitable for producing such lenses, preferably are used. The aberration correction may be on either or both the front or back surface of the ophthalmic lens.

The contact lenses also may incorporate an inverse topographic elevation map of the lens wearers' cornea on the front, or object-side, surface or the back, or eye-side, surface. The corneal topography of the individual may be determined by any known method including, without limitation, by use of a corneal topographer. For soft contact lens manufacture, the elevational data initially is applied to a lens model in the unflexed state. Next, the data is transformed by taking into account the soft lens flexure, or wrap, when the lens placed on the eye. Thus, the effects of both elevation of the cornea and wrap are accounted for when using the corneal topographic data. The flexure transformed data then may be mapped onto a CNC grid pattern and used to make the lenses or mold tool surface.

The ophthalmic lenses of the invention may be made by any known means for ophthalmic lens manufacture. For example, contact lenses of the invention may be formed by any conventional method including, without limitation, diamond-turning of molds that are used to form the lens of the invention. Subsequently, a suitable liquid resin is placed between the molds followed by compression and curing of the resin to form the lenses of the invention. Alternatively, the contact lenses surfaces may be diamond-turned into lens buttons.

Any known materials suitable for manufacturing ophthalmic lenses may be used to manufacture the lenses of the invention. For the preferred, contact lens, embodiment, the materials useful for forming the lenses of the invention may be any known materials used in the production of hard or soft contact lenses. Preferably, the material selected for forming the lenses of the invention is a material suitable for forming soft contact lenses. Suitable materials for forming such contact lenses using the method of the invention include, without limitation, silicone elastomers, silicone-containing macromers including, without limitation, those disclosed in U.S. Pat. Nos. 5,371,147, 5,314,960, and 5,057, 578 incorporated in their entireties herein by reference, hydrogels, silicone-containing hydrogels, and the like and combinations thereof More preferably, the surface is a siloxane, or contains a siloxane functionality, including, without limitation, polydimethyl siloxane macromers, methacryloxypropyl polyalkyl siloxanes, and mixtures thereof, silicone hydrogel or a hydrogel, such as etafilcon A.

What is claimed is:

1. A method for designing a correction for an individual's visual acuity, comprising the steps of: a.) obtaining, for a computationally sufficient amount of time, an ocular wavefront aberration measurement of the individual's eye; b.) determining a frequency component and an amplitude component for cyclical variations of the ocular wavefront aberration measurements; and c.) computing an ocular wavefront aberration correction for one or more aberrations of the individual's eye taking into account -the cyclical variations.

2. The method of claim 1, wherein the computationally sufficient amount of time is a time necessary for completion of one biophysical cycle.

3. The method of claim 1, wherein step b.) is carried out by: i.) representing the ocular wavefront aberrations as Zernike coefficients; ii.) subjecting the Zernike coefficients to a fast Fourier transform; and iii.) assembling the transform values into a histogram.

4. The method of claim 1, wherein step c.) further comprises incorporating changes in the elevation of a lens' front surface, back surface, or a combination thereof to achieve correction of the ocular wavefront aberrations.

5. The method of claim 1, further comprising step d.) matching the back surface of a lens to a corneal topography of the individual.

6. The method of claim 5, further comprising incorporating changes in the elevation of a lens' front surface to achieve correction of the ocular wavefront aberrations.

7. A contact lens produced by the method of claim 6.

8. A contact lens produced by the method of claim 5.

9. The method of claim 1, further comprising step d.) matching the front surface of a lens to a corneal topography of the individual.

10. The method of claim 9 further comprising incorporating changes in the elevation of a lens' front surface to achieve correction of the ocular wavefront aberrations.

11. A contact lens produced by the method of claim 10.

12. A contact lens produced by the method of claim 9.

13. An ophthalmic lens produced by the method of claim 1.

14. A contact lens produced by the method of claim 1.

* * * * *